United States Patent [19]

Isaacson

[11] Patent Number: 5,573,510
[45] Date of Patent: Nov. 12, 1996

[54] SAFETY INTRAVENOUS CATHETER ASSEMBLY WITH AUTOMATICALLY RETRACTABLE NEEDLE

[76] Inventor: Dennis R. Isaacson, 239 Wymount Ter., Provo, Utah 84604

[21] Appl. No.: 315,880

[22] Filed: Sep. 30, 1994

Related U.S. Application Data

[63] Continuation-in-part of Ser. No. 202,729, Feb. 28, 1994, abandoned.

[51] Int. Cl.$^6$ .................................................. A61M 5/178
[52] U.S. Cl. ........................... 604/158; 604/164; 604/198
[58] Field of Search .................................... 604/164, 165, 604/158, 168, 171, 263, 264, 272, 198

[56] References Cited

U.S. PATENT DOCUMENTS

| | | | |
|---|---|---|---|
| 4,160,450 | 7/1979 | Doherty . | |
| 4,316,463 | 2/1982 | Schmitz et al. | 128/218 F |
| 4,542,749 | 9/1985 | Caselgrandi et al. | 128/752 |
| 4,747,831 | 5/1988 | Kulli | 604/110 |
| 4,838,869 | 6/1989 | Allard | 604/195 |
| 4,850,968 | 7/1989 | Romano | 604/110 |
| 4,874,382 | 10/1989 | Lindemann et al. | 604/195 |
| 4,887,998 | 12/1989 | Martin et al. | 604/110 |
| 4,894,055 | 1/1990 | Sudnak | 604/198 |
| 4,900,307 | 2/1990 | Kulli | 604/110 |
| 4,904,242 | 2/1990 | Kulli | 604/110 |
| 4,927,414 | 5/1990 | Kulli | 604/110 |
| 4,936,830 | 6/1990 | Verlier | 604/110 |
| 4,941,883 | 7/1990 | Venturini | 604/186 |
| 4,966,593 | 10/1990 | Lennox | 604/198 |
| 4,973,316 | 11/1990 | Dysarz . | |
| 4,978,343 | 12/1990 | Dysarz et al. . | |
| 4,994,034 | 2/1991 | Botich et al. | 604/110 |
| 5,013,301 | 5/1991 | Marotta, Jr. et al. | 604/197 |
| 5,017,187 | 5/1991 | Sullivan | 604/110 |
| 5,019,044 | 5/1991 | Tsao | 604/110 |
| 5,049,133 | 9/1991 | Pascual | 604/110 |
| 5,053,010 | 10/1991 | McGary et al. | 604/110 |
| 5,064,419 | 11/1991 | Gaarde | 604/195 |
| 5,069,667 | 12/1991 | Freundlich et al. | 604/110 |
| 5,085,640 | 2/1992 | Gibbs | 604/110 |
| 5,088,986 | 2/1992 | Nusbaum | 604/195 |
| 5,092,853 | 3/1992 | Couvertier, II . | |
| 5,102,394 | 4/1992 | Lasaitis et al. | 604/164 |
| 5,112,307 | 5/1992 | Haber et al. | 604/110 |

(List continued on next page.)

*Primary Examiner*—John D. Yasko
*Attorney, Agent, or Firm*—Workman, Nydegger & Seeley

[57] ABSTRACT

A safety intravenous catheter assembly is provided by interconnecting a safety receptacle for a retractable intravenous needle with a catheter that carries the needle and is advancible into a vein punctured by the needle. A coupling that is removably fastened to the catheter has an elongate stem portion that extends backwardly into the safety receptacle past a needle-stopping member within such receptacle. Such needle-stopping member is active to normally prevent backward movement of the needle into the receptacle. However, ultimate forward movement of the coupling with respect to the needle-stopping member following catheter emplacement into the vein permits movement of such needle-stopping member to non-stopping position, so that a tensioned spring can automatically urge the needle backwardly to a position wholly within the safety receptacle that protects against any accidental pricking, whereupon such receptacle, with its protectively contained needle, is discardable following removal of the coupling and the protectively encased needle from the emplaced catheter to prepare the catheter for IV connection and to prevent reuse of the contaminated needle.

The needle-stopping member may be a stop gate that is cammed into open position or that is provided with a spring tensioned to open the gate when the rearward end of the coupling stem has passed through it in the manual advancement of the catheter into emplaced position in a vein of a patient. However, the presently contemplated best mode is to provide the needle-stopping member as a latching member carried by the needle stem, slidable within the safety receptacle, and arranged to be normally latched into needle-stopping position.

12 Claims, 7 Drawing Sheets

U.S. PATENT DOCUMENTS

| | | | |
|---|---|---|---|
| 5,114,404 | 5/1992 | Paxton et al. | 604/110 |
| 5,114,410 | 5/1992 | Batlle | 604/195 |
| 5,120,308 | 6/1992 | Hess | 604/95 |
| 5,120,310 | 6/1992 | Shaw | 604/110 |
| 5,122,118 | 6/1992 | Haber et al. | 604/110 |
| 5,125,414 | 6/1992 | Dysarz . | |
| 5,129,884 | 7/1992 | Dysarz . | |
| 5,147,303 | 9/1992 | Martin | 604/110 |
| 5,163,918 | 11/1992 | Righi et al. | 604/198 |
| 5,167,641 | 12/1992 | Schmitz | 604/196 |
| 5,176,650 | 1/1993 | Haining | 604/164 |
| 5,180,369 | 1/1993 | Dysarz | 604/110 |
| 5,180,370 | 1/1993 | Gillespie | 604/110 |
| 5,186,712 | 2/1993 | Kelso et al. | 604/165 |
| 5,188,599 | 2/1993 | Botich et al. | 604/110 |
| 5,188,613 | 2/1993 | Shaw | 604/195 |
| 5,190,526 | 3/1993 | Murray et al. | 604/110 |
| 5,376,075 | 12/1994 | Haughton et al. | 604/158 |
| 5,382,237 | 1/1995 | Daugherty | 604/164 |

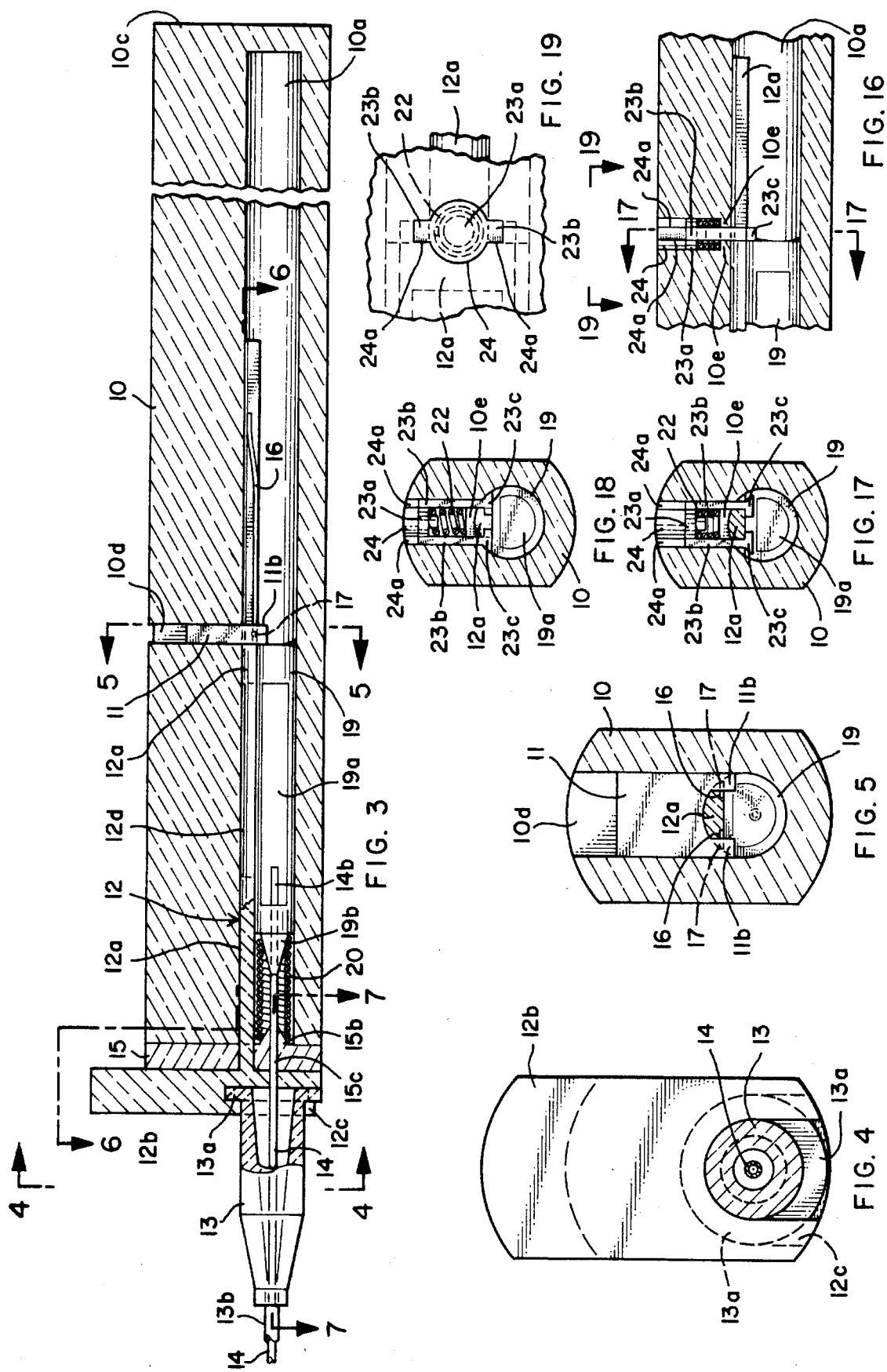

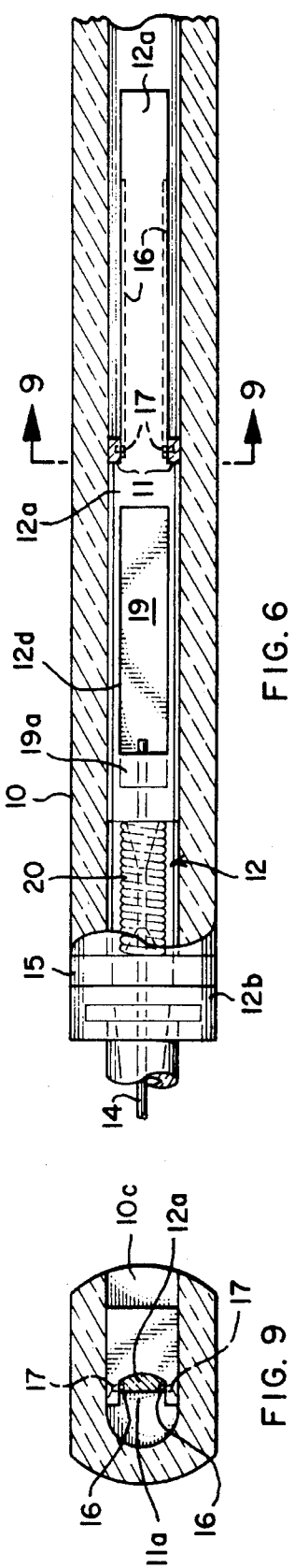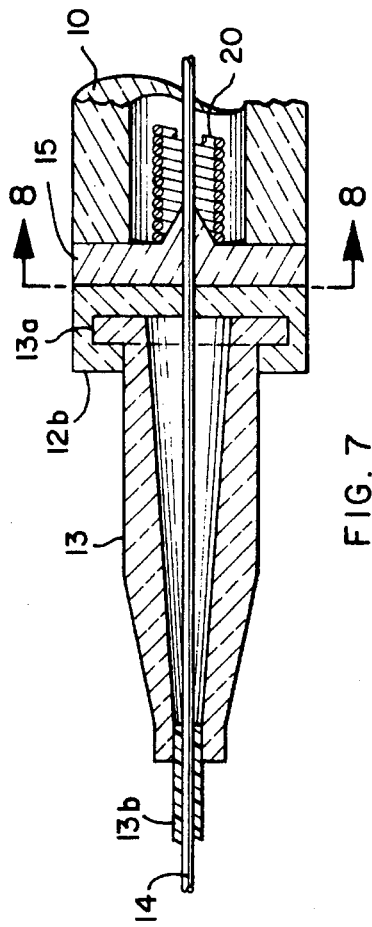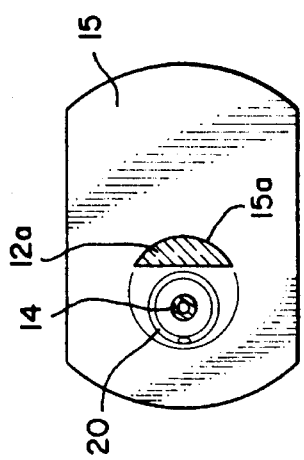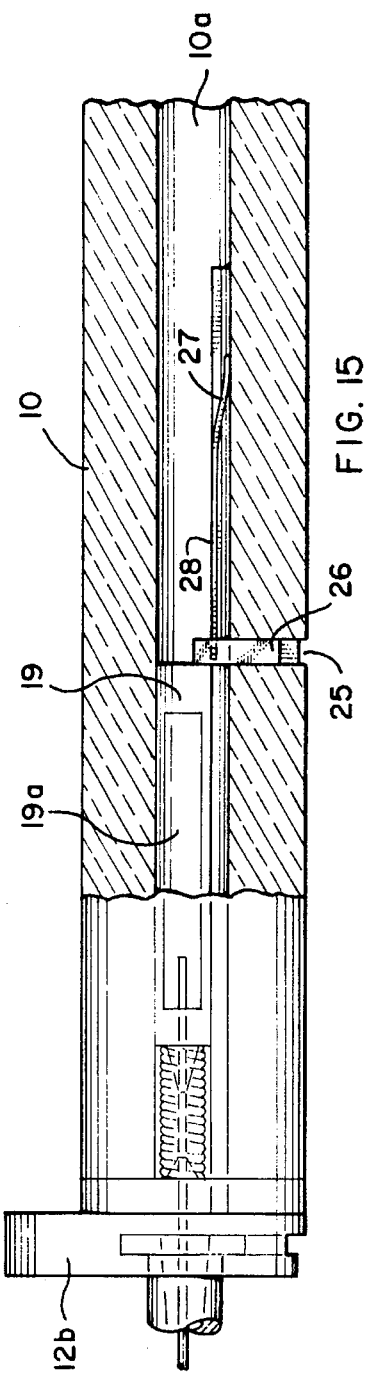
FIG. 6
FIG. 7
FIG. 8
FIG. 9
FIG. 15

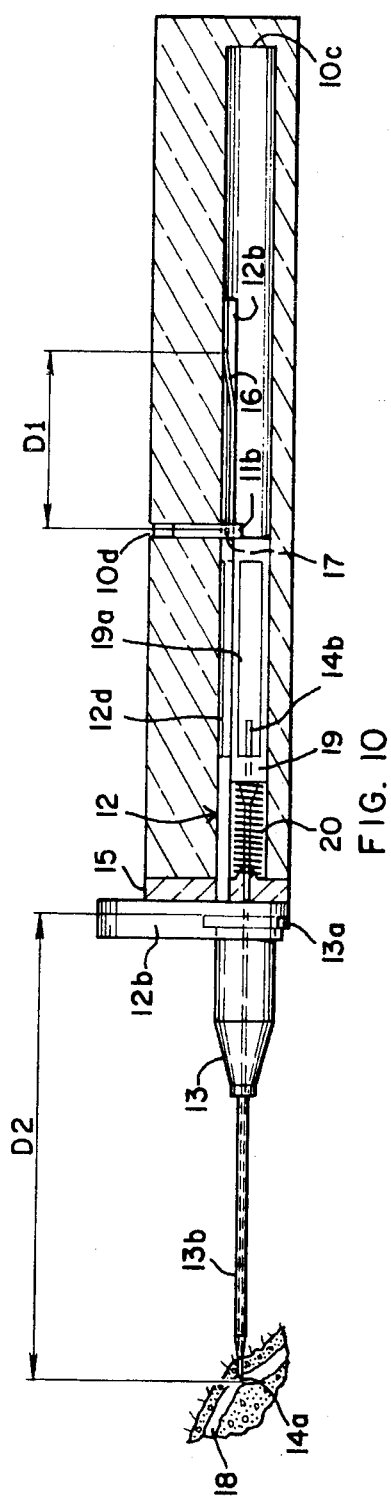
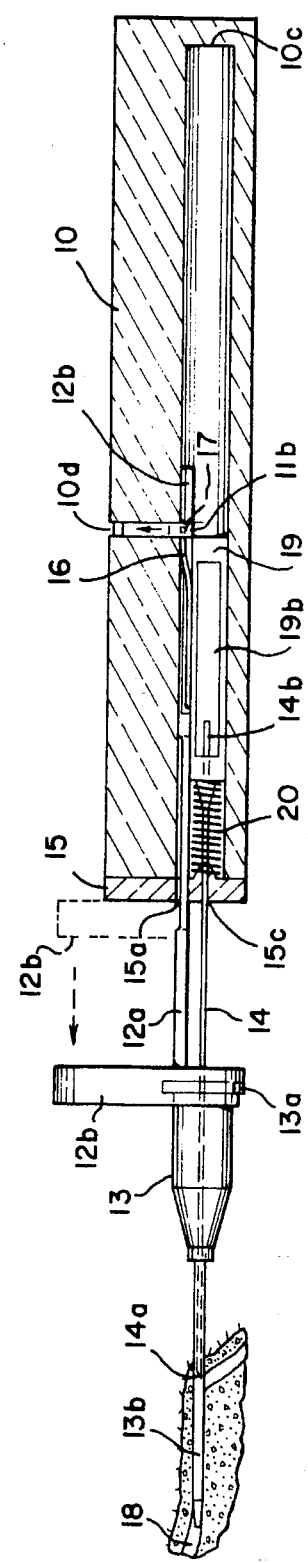
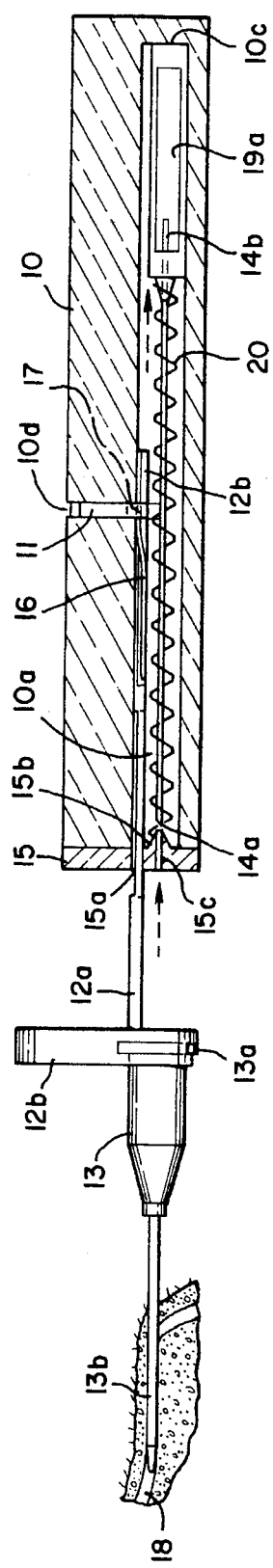

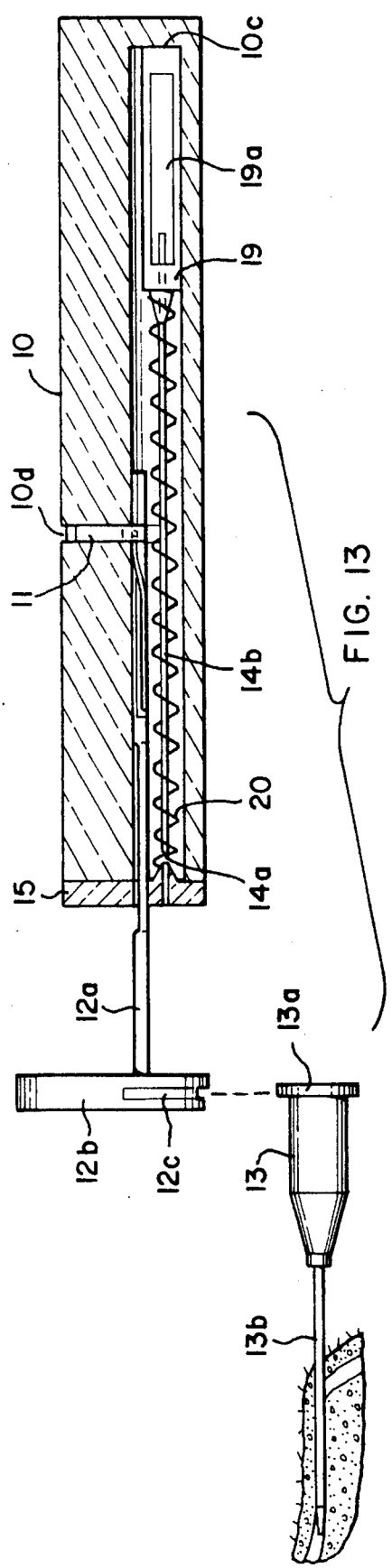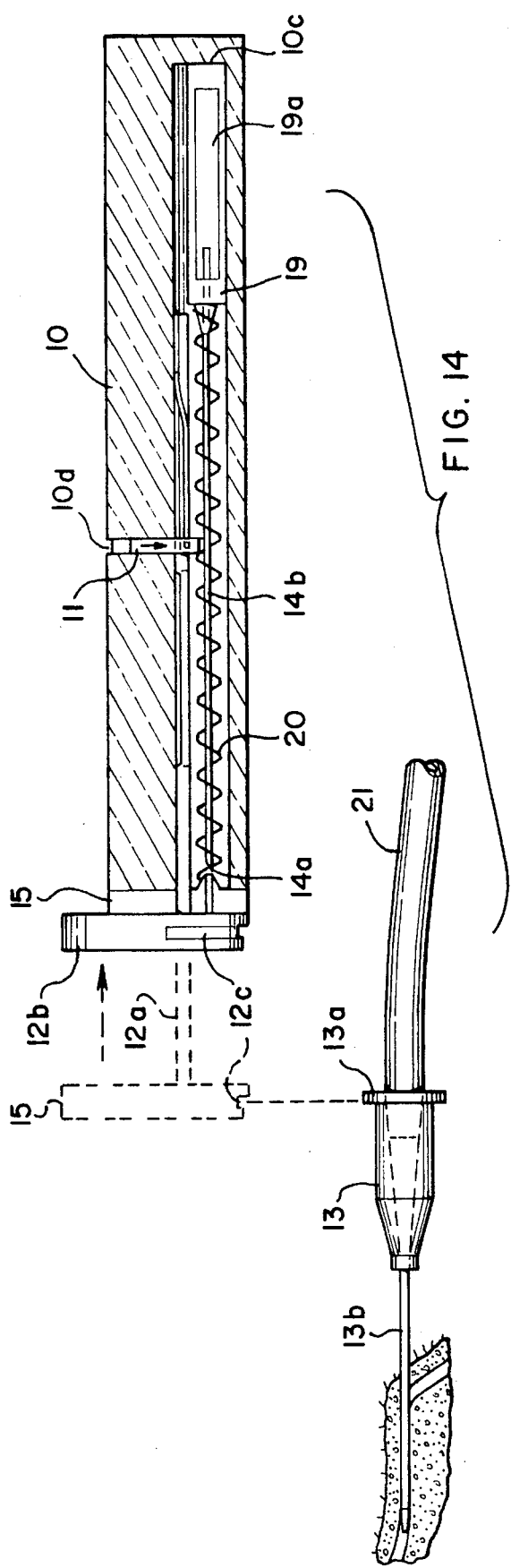

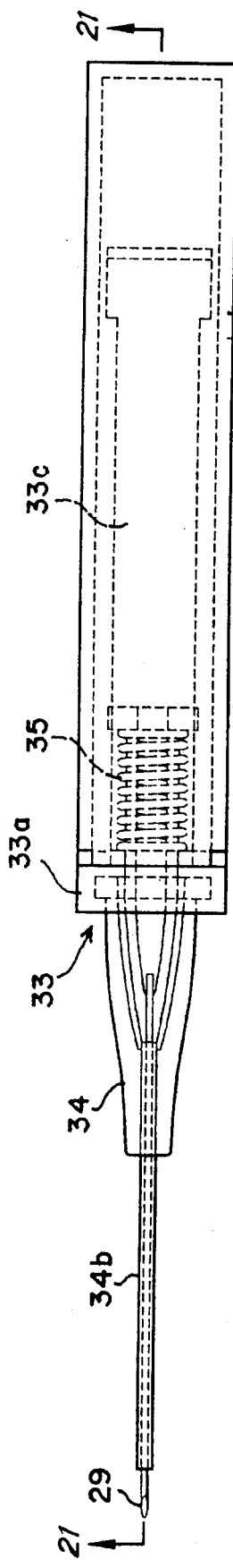
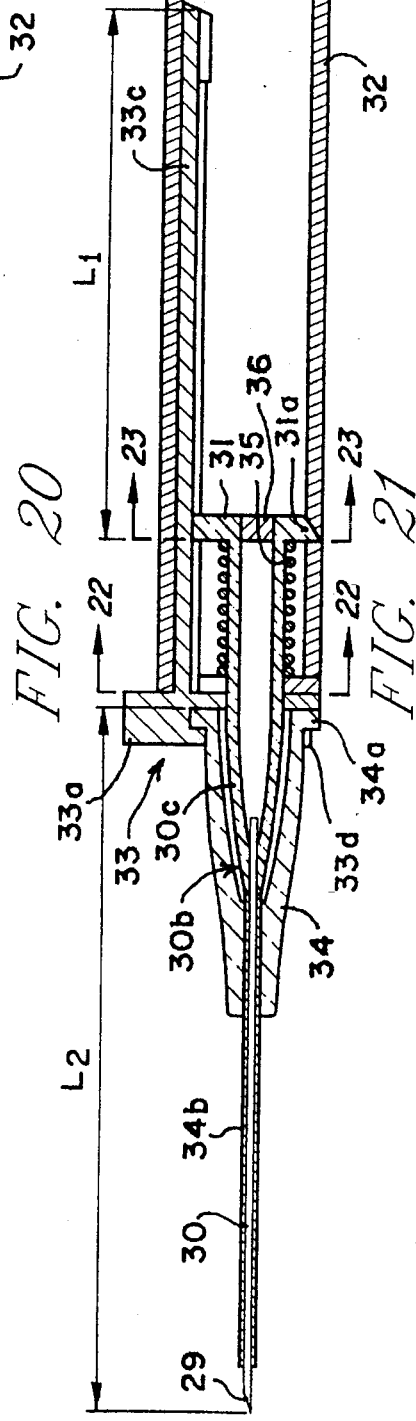
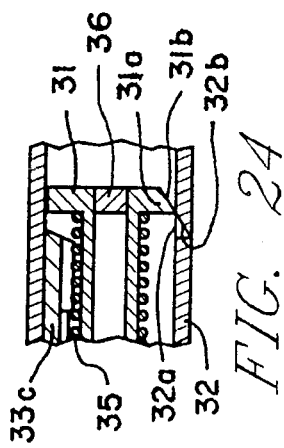
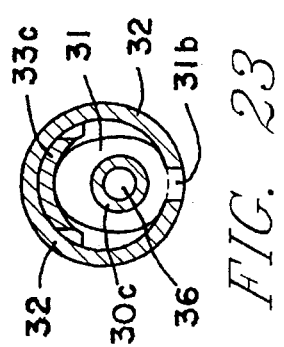
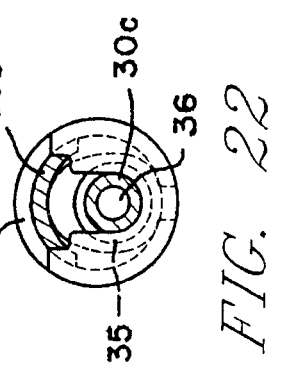

SAFETY INTRAVENOUS CATHETER ASSEMBLY WITH AUTOMATICALLY RETRACTABLE NEEDLE

Prior Application

The present application is a continuation-in-part of allowed, application Ser. No. 08/202,729, filed Feb. 28, 1994, now abandoned.

BACKGROUND OF THE INVENTION

1. Field

The invention is in the field of venipuncture needles whose puncture points protrude from respective catheters which are to be placed in a vein punctured by the needle, and relates particularly to such venipuncture needle/catheter combinations in which the needle is retractable, following catheter placement, as a safety precaution against accidental pricking of the user following use, as well as to prevent reuse of a contaminated needle.

2. Prior Art

The prior art in this field is well-developed so far as needle retractability is concerned, but is very limited from the standpoint of automatic release of the needle for retraction following venipuncture and placement of the catheter in the vein.

An early patent to George O. Doherty, Missoula, Mont., U.S. Pat. No. 4,160,450 of Jul. 10, 1979, discloses venipuncture needle retractability within a safety chamber formed as a needle-receiving portion of the catheter.

Several later patents to Edward D. Dysarz of Houston, Tex., namely, U.S. Pat. No. 4,973,316 of Nov. 27, 1990, U.S. Pat. No. 5,125,414 of Jun. 30, 1992, and U.S. Pat. No. 5,129,884 of Jul. 14, 1992, disclose various arrangements for retracting an intravenous needle in an hypodermic syringe by spring action, as does a patent to Douglas Couvertier, II of Fort Lauderdale, Fla., U.S. Pat. No. 5,092,853, issued Mar. 3, 1992. The latter also purports to show embodiments of a device for placing a catheter in a vein.

Despite these developments in the field of medical needle retractability for safety purposes, there remains a need for preventing withdrawal of the needle from the catheter before activating needle release mechanism and while allowing the catheter to be maneuvered back and forth along and around the needle to facilitate deep placement of the catheter in the vein.

SUMMARY OF THE INVENTION

In accordance with the present invention, I have provided elongate coupling means between the hub of an intravenous catheter, through which the needle extends, and a separate, safety, needle-retraction receptacle. One end of the coupling, which is forward from the standpoint of needle insertion in a vein, is formed as a catheter-engagement member and is placed across the longitudinal axis of the coupled needle and safety receptacle, preferably as an upwardly protruding, finger-engagement tab, while an elongate stem of the coupling extends into and longitudinally along the needle-receiving chamber of the safety receptacle for needle unblocking coaction with needle-stopping means positioned within such chamber.

In one embodiment of the invention, the coupling stem is formed with a camming trackway for automatically camming the needle-stopping member, here a stop gate, to move it from needle-stopping position to an out-of-the-way position. The needle-stopping member, i.e., stop gate, is positioned internally of the safety receptacle and is slidably mounted in a wall thereof to extend transversely across the interior of the receptacle for preventing rearward, retractive movement of the needle. Less desirably, in an alternative embodiment of the invention, the stop gate is spring-activated, rather than being cammed, to automatically move to a position that permits automatic retraction, i.e. backward movement, of the needle to safety position within the needle-receiving chamber of the safety receptacle. However, the best mode now presently contemplated is to have the needle-stopping member carried rigidly by the rear end portion of the needle stem for initially releasibly latching into the safety receptacle and for unlatching by reason of forward movement of the coupling stem while placing the catheter in the vein, followed by backward movement of the safety receptacle, carried out manually, for withdrawing the needle from the catheter, thereby effecting unlatching.

In all embodiments, it is important that the length of the coupling stem be such that the distance between the release point of the needle-stopping member and the needle release actuating point on the rearward end portion of such coupling stem be shorter than the distance between the rearward end of the catheter and the sharp venipuncturing tip of the needle when the catheter and the coupling are in the initial unextended position in order to insure that the used needle tip will be covered by the catheter until the needle release has been effected.

The coupling is made up of a forward, catheter-engaging member and a rearwardly-extending stem. It securely holds the catheter with the needle extending transversely across the line of separation between catheter and coupling member so as to serve as a barrier to catheter separation until the needle is completely withdrawn from the catheter, which occurs only after the needle release has been automatically activated.

In the presently preferred embodiment, a flash chamber for blood to reveal whether an initial venipuncture has been successful is located at least partially in advance of the safety receptacle which is normally gripped by the user.

THE DRAWINGS

Several embodiments of the invention are illustrated in the accompanying drawings, in which:

FIG. 1 is a perspective view of one embodiment of the safety intravenous catheter of the invention ready for use;

FIG. 2, an exploded view of that embodiment;

FIG. 3, a side elevation, largely in longitudinal, vertical section taken on the line 3—3 of FIG. 1, an intermediate longitudinal portion thereof and the sharp tip of the needle being broken out for convenience of illustration;

FIG. 4, a transverse, vertical section, partially in front elevation, taken along the line 4—4 of FIG. 3;

FIG. 5, a transverse vertical section taken along the line 5—5 of FIG. 3;

FIG. 6, a fragmentary top plan view largely in horizontal section taken along the line 6—6 of FIG. 3;

FIG. 7, an enlarged, fragmentary horizontal section taken along the line 7—7 of FIG. 3;

FIG. 8, a transverse vertical section taken along the line 8—8 of FIG. 7;

FIG. 9, a transverse vertical section taken along the line 9—9 of FIG. 6;

FIG. 10, a view largely corresponding to that of FIG. 3 but drawn to a somewhat smaller scale and showing an initial venipuncture, with catheter-encased portions of the needle appearing in broken lines;

FIG. 11, a similar view but showing the forward end of the catheter emplaced deeply into the patient's vein;

FIG. 12, a similar view but showing the needle as automatically fully retracted into the needle-retraction chamber of the safety receptacle under spring pressure;

FIG. 13, a view corresponding to that of FIG. 12, but showing the safety retraction receptacle with its protectively encased needle and the coupling lifted free of the vein-emplaced catheter;

FIG. 14, a view corresponding to that of FIG. 13 but showing the coupling as having been manually pushed backwardly into abutting relationship with the front of the safety retraction receptacle from its position in FIG. 13, which is here indicated by broken lines;

FIG. 15, a fragmentary enlarged view in side elevation and partially in axial section with respect to what is presently contemplated as a less desirable but alternative embodiment, wherein the positions of the stop gate and of the elongate stem of the coupling are reversed;

FIG. 16, a fragmentary, longitudinal, vertical section corresponding to an intermediate portion of FIG. 3, but showing what is presently contemplated as a less desirable but alternative form of stop gate arrangement for the embodiment of FIGS. 1–14;

FIG. 17, a transverse vertical section taken on the line 17—17 of FIG. 16 showing needle retraction blocked by the stop gate in its lowered portion;

FIG. 18, a view corresponding to that of FIG. 17 but showing needle retraction automatically unblocked;

FIG. 19, a fragmentary top plan view of the fragmentary portion shown in FIG. 16;

FIG. 20, a top plan view of an embodiment presently contemplated as being the best mode of carrying out the invention in actual practice, internal structure being shown by broken lines;

FIG. 21, a view in axial vertical section taken on the line 21—21 of the embodiment of FIG. 20;

FIG. 22, a view in transverse section taken on line 22—22 of FIG. 21;

FIG. 23, a similar view taken on the line 23—23 of FIG. 21; and

FIG. 24, an enlarged, fragmentary, intermediate portion of FIG. 21 shown immediately after unlatching of the needle-stopping member so the needle can be automatically retracted into the safety receptacle.

DETAILED DESCRIPTION OF THE ILLUSTRATED EMBODIMENTS

Figure 1:
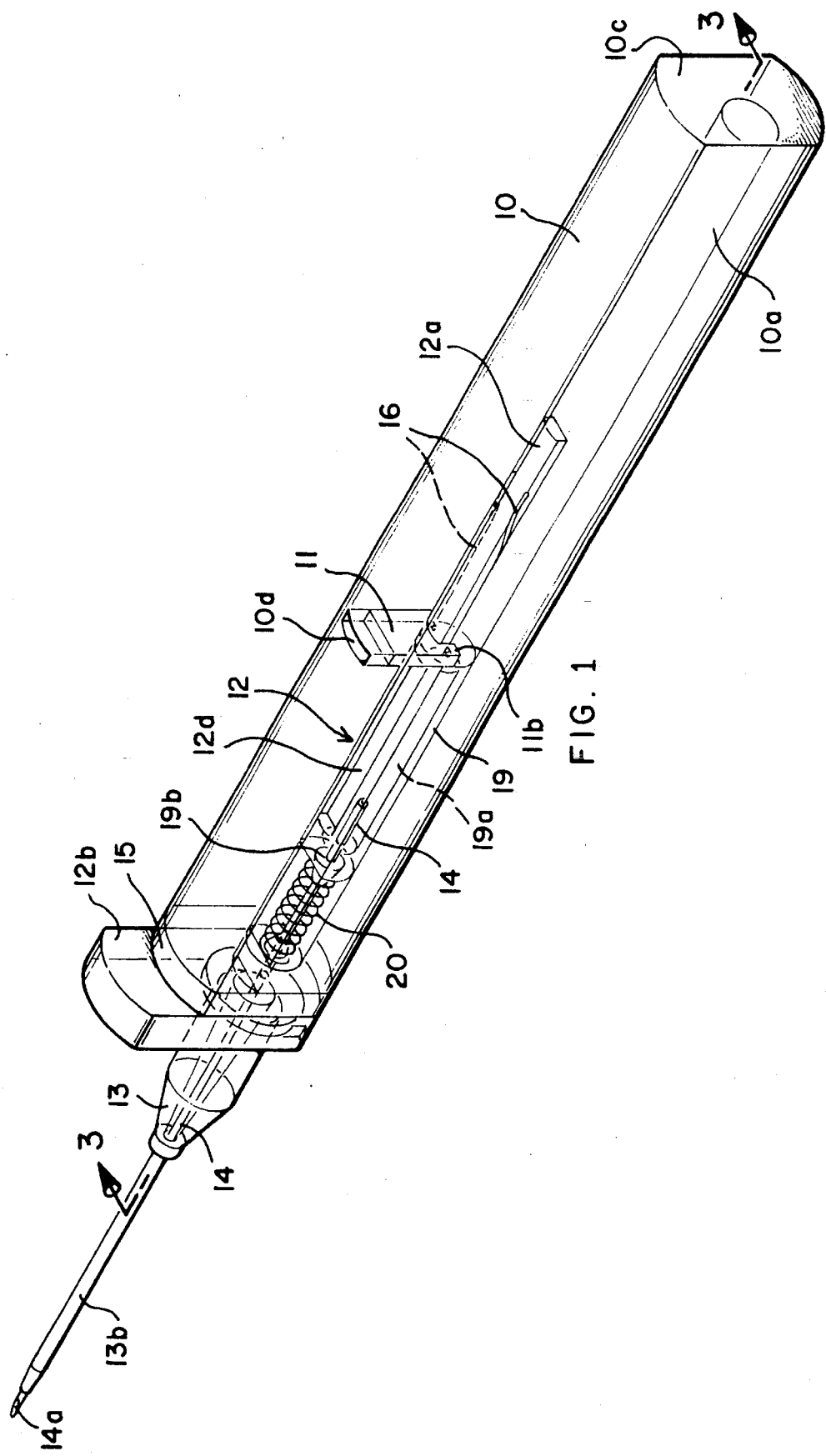
Figure 2:
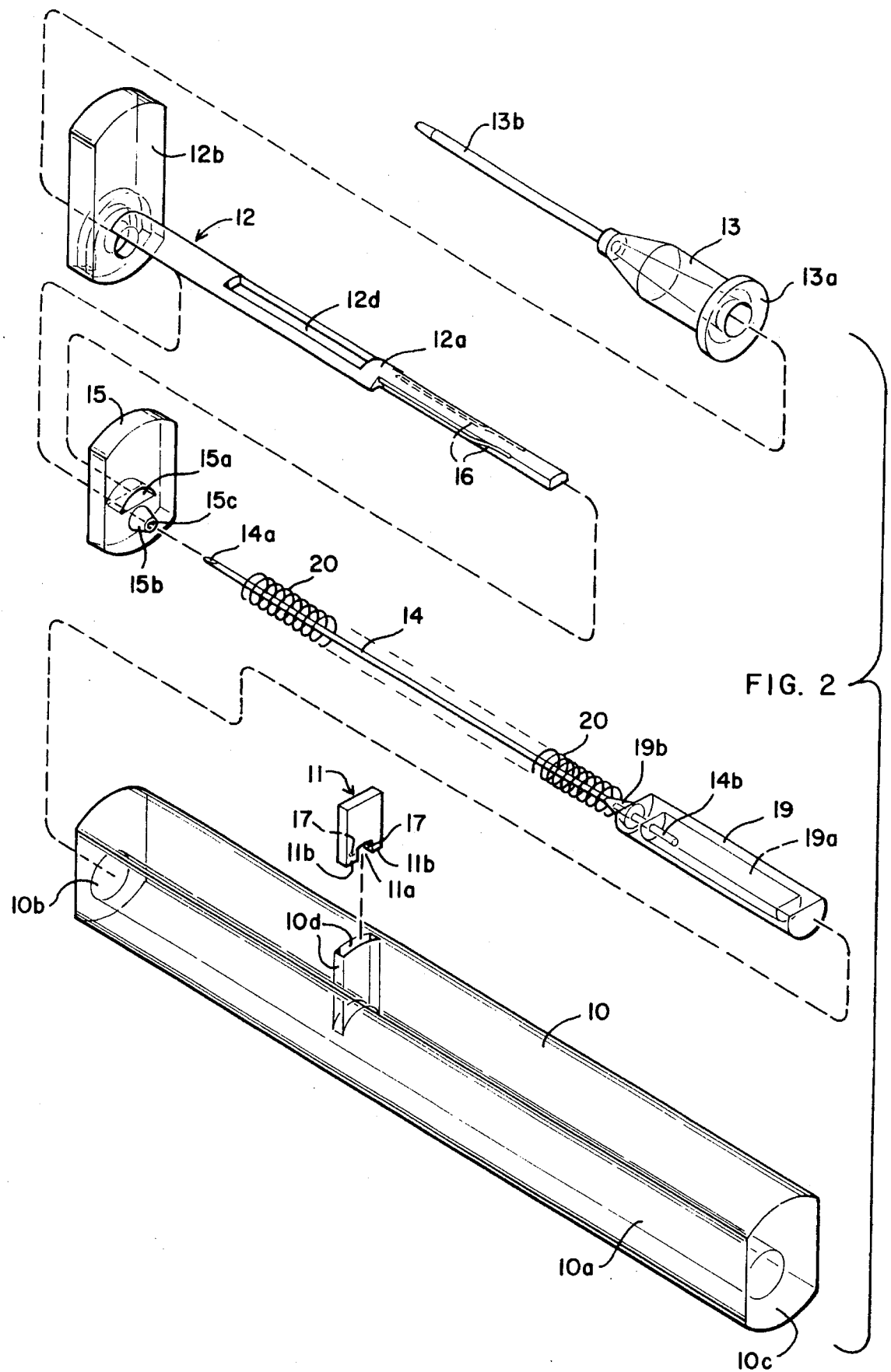

The embodiment of FIGS. 1–14 is shown as assembled from various parts molded in customary fashion from a plastic material such as a polyethylene. Thus, an elongate, safety, needle-retraction receptacle 10, FIG. 2, is molded preferably from a transparent plastic material to provide see-through, solid walls defining an elongate, cylindrical, needle-receiving chamber 10a parallel with the longitudinal axis of such receptacle and having an opening 10b, FIG. 2, at one end thereof, being closed at the opposite end 10c thereof, and having a transverse slot 10d intermediate the length thereof which, in the preferred orientation of the device when used, extends downwardly from the upper surface of such receptacle 10 to intersect with and across the width of the cylindrical chamber 10a. Slidably positioned for up and down movement in slot 10d is needle-stopping means in the form of a stop gate 11 of inversed U formation through which passes, unimpeded, an elongate stem member 12a of an elongate coupling 12, FIGS. 1, 2, 3, and 6, between and normally interconnecting an intravenous catheter 13 and safety receptacle 10 for a vein-puncturing needle 14 when it is retracted.

For enabling easy and convenient introduction of needle and catheter intravenously in a medical patient, see FIGS. 10–12, followed by manual separation of the assembled coupling 12, safety receptacle 10, and encased needle 14 with venipuncturing point 14a and stem 14b from catheter 13, FIG. 13, coupling 12 has an elongate stem member 12a extending backwardly from a forward, catheter-engaging member 12b preferably in the form of an upstanding push tab. Coupling member 12a is adapted to slidably receive, by means of a slideway 12c, FIG. 4, the flanged hub end 13a of catheter 13, whereby coupling 12 can be quickly and easily separated from the catheter or vice versa.

Stem member 12a of coupling 12 extends backwardly through a receiving opening 15a, FIG. 2, in an end closure 15 for receptacle 10 and through opening 10b of receptacle 10 into needle safety chamber 10a, see especially FIG. 3, and, for this embodiment, is provided laterally along opposite sides of a reduced width rear end portion thereof, see FIG. 2, with respective, elongate, camming slots 16. Fitted into such camming slots are respective cam pins 17, FIGS. 2 and 5, that project internally of the widely open lower end 11a of stop gate 11 and serve to push up stop gate 11 into non-blocking position, FIGS. 11 and 12, when the forward end 13b of catheter 13 is pushed into a vein 18, FIG. 11, of a patient by means of either the push tab 12b following penetration of the vein by the point 14a of needle 14, FIG. 10, or merely when the person holding the device by means of receptacle 10 pushes such receptacle forwardly.

Needle 14 is hollow as usual and is sufficiently elongate to extend backwardly of catheter 13 through the open, flanged, hub end 13a thereof, FIGS. 3 and 7, into receiving chamber 10a of safety receptacle 10, passing through a receiving opening 15c, FIG. 12, in the otherwise closed lower portion of receptacle end closure 15 and through the opening 10b, FIG. 2, in the corresponding end of receptacle 10, and terminating in an elongate needle stem 14b made up of a transparent, blood-receiving receptacle 19 having a flash chamber 19a therewithin, such receptacle 19 being slidable within and along chamber 10a of safety receptacle 10 but being normally stopped by the feet 11b, FIGS. 3, 5, and 10, of lowered stop gate 11 against which it normally abuts.

It should be noted that coupling stem 12a is made from either a transparent plastic or is provided with a window 12d, so it can be observed through the transparent body of safety receptacle 10 whether blood is flowing into flash chamber 19a that is indicative of a successful venipuncture.

Normally, compressed between the forward end of blood-receiving receptacle 19 and the inner face of safety receptacle end closure 15, which has a tapered, rearwardly projecting, spring-anchoring projection 15b surrounding an opening 15c, FIGS. 2, 3, and 12, through which needle stem 14b passes, is a normally compressed, coil spring 20, the forward end of receptacle 19 preferably being tapered forwardly and projecting forwardly, as at 19b, corresponding to the tapering of projection 15b but in reverse, for anchoring such spring 20 in its extension backwardly, FIG. 2, when permitted to do so by the cammed raising of stop gate 11 as previously explained. In its extension backwardly, spring 20 automatically forces blood-receiving receptacle 19 of needle stem 14b and the entire length of the needle and needle stem backwardly, as shown in FIG. 12, wherein the sharp point 14a of the needle is safely encased within needle-receiving chamber 10a of safety receptacle 10.

Following this, coupling 12 and receptacle 10 are lifted free of the emplaced catheter 13, as shown in FIG. 13, and supply tubing 21 from the usual bottle of I.V. solution (not shown) is attached to the hub 13a of catheter 13 as shown in FIG. 14.

What is presently regarded as a less desirable way of unblocking rearward movement of needle 14 and needle stem 14b is shown in FIGS. 16–19, wherein, in place of the camming arrangement aforedescribed, a normally compressed coil spring 22 is received by a corresponding cylindrical bore in safety receptacle 10 and by the underside of a cylindrical top portion 23a of a stop gate 23 that replaces stop gate 11 of the foregoing embodiment. Stop gate 23 is raised by a spring 22 from its stop position of FIGS. 16 and 17, where it blocks backward movement of the needle 14 (not here shown) and of the blood-receiving receptacle 19, to the unblocking position of FIG. 18 in which blood-receiving receptacle 19 is permitted to pass under stop gate 23 and into abutment against the closed end 10d of safety receptacle 10 under the impetus of spring 20.

In this embodiment, stop gate 23 is of a somewhat different inverted U-shape, with a cylindrical top 23a and legs 23b depending therefrom. Feet 23c, FIG. 17, project inwardly of the inverted U and outwardly thereof to stop rearward travel of needle 14 and of its blood-receiving receptacle 19 when gate 23 is in the down position of FIGS. 16 and 17. The legs 23b of stop gate 23 fit into and slide within lateral extensions 24a of a cylindrical slideway 24, see FIGS. 16 and 19, provided by a bore in safety receptacle 10. The lower end of spring 22 rests on shelf portions 10e, FIG. 16, of safety receptacle 10, thereby enabling such spring to automatically push up stop gate 23 when catheter 13 is pushed forwardly into the vein, as shown in FIG. 11, coupling stem 12a being moved forwardly through stop gate 23 from the blocked position of FIGS. 16 and 17 until it passes entirely through to permit such gate to rise in its slideways 24 and 24a. Thus, spring 20 is able to move needle 14 and blood-receiving receptacle 19 of needle stem 14b backwardly so that the point 14a of needle 14 is in the retracted safety position of FIG. 12. In this position of needle 14, receptacle 10, with coupling 12, can be lifted free of the emplaced catheter 13, see FIG. 13, and discarded as previously described with respect to the first embodiment of FIGS. 1–14, normally but not necessarily after pushing coupling 12 backwardly so push tab 12b abuts the forward end of safety receptacle 10, as in FIG. 14.

It should be noted that, as previously indicated, spring 22 extends between shelf members provided for this embodiment at the bottom of stop-gate-receiving slideway 24 as a stationary rest for the lower end of spring 22 and the feet members 23c of stop gate 23, so that, when coupling stem 12a is moved forwardly and out from the stop gate, and spring 22 raises stop gate 23, the feet members 23b thereof abut against the overhanging, interior-defining surfaces of safety cylinder 10 and prevent further rising of stop gate 23 under the impetus of spring 22.

As shown in FIG. 15, the arrangement of coupling stem and stop gate could, less desirably as presently contemplated, be altered so that stop gate slideway (here designated 25) is at the bottom of the needle safety receptacle 10 when the device is held for venipuncture. The stop gate (here designated 26) is automatically lowered, by the inversely-formed camming slot (here designated 27) of the coupling stem (here designated 28), or by a spring corresponding to the spring 22 if used, instead of being lifted as in the first embodiment of FIGS. 1–14 or as in the second embodiment of FIGS. 16–19.

The best mode presently contemplated in accordance with this continuation-in-part application is shown in newly added FIGS. 20 through 24. However, all embodiments of the invention are unique in providing automatic activation of needle release for automatic retraction of the venipuncturing needle.

The earlier embodiments of this invention provide for carrying out the desired automatic retraction by releasably coupling the intravenous catheter and the safety receptacle together and providing needle-stopping means in the form of a stop gate through which a rearward stem of the releasable coupling means extends. Means are provided for moving the gate out of stop position upon forward movement of the coupling stem to or beyond a set limit. The present embodiment similarly provides for moving a needle-stopping member out of stopping position, but does so by a simpler structural arrangement wherein the needle stem carries a needle-stopping member for latching into the safety receptacle.

As illustrated in FIGS. 20 through 24, a needle 30, having a sharp, venipuncturing point 30a and a rearwardly extending needle stem 30b, with blood-receiving receptacle 30c, carries, normally at the rear end of needle stem 30b, a needle-stopping member 31, which serves, as do the stop gates 11, 23, and 26 of the earlier embodiments, to prevent rearward travel of the needle until automatically released to permit rearward travel that retracts its sharp point 30a into a safety receptacle 32.

As in the earlier embodiments, a coupling means 33 has a forward coupling member 33a, normally and preferably in the form of an upstanding tab portion, and has a coupling stem portion 33c that extends rearwardly into and along safety receptacle 32. Coupling means 33 serves to connect a catheter 34 with safety receptacle 32, the rearward end of catheter 34 being provided with a flange 34a that slidably engages a receiving groove 33d in forward coupling member 33a.

Needle-stopping member 31 is needle-stopping by reason of a projecting latch member 31a that is normally interengaged with a receiving recess 32a, FIG. 24, formed in the wall of safety receptacle 32 and opening into its inner surface. Latch member 31a is normally pressed into latching recess 32a, FIG. 21, by coupling stem 33c.

After catheter emplacement, as in FIG. 11 of the earlier embodiments, the needle safety receptacle 32 is moved backwardly, while the stem forward portion 34b of catheter 34 is held in place so that the needle from the catheter 30 is withdrawn by reason of latch member 31a being in latching position. Thus, coupling stem 33c ultimately becomes positioned forwardly of needle-stopping member 31, see FIG. 24, thereby automatically releasing the latching of needle-stopping member 31 and permitting spring 35 to automatically force the entire needle assembly, including needle-stopping member 31, backwardly to disengage latch member 31a from latching recess 32. The provision of upwardly and backwardly sloping ramp surfaces 31b and 32b of latch member 31a and latch recess 32a respectively FIG. 24, facilitates disengagement of the latch members under the backward urge of spring 35, which backward urge continues to automatically move needle 30 and its rearward extension 31 rearwardly until needle-stopping member 31 abuts end wall 32c of safety receptacle 32. With needle 30 completely within safety receptacle 32 and its sharp point 30a completely covered during separation of safety receptacle 32 and its encased needle 30 from catheter 34 and disposal of both the needle and its safety receptacle.

It should be noted that needle stem 30b and catheter 34 should be fabricated from a transparent material so blood-receiving receptacle 30c will serve as a flash chamber. Even though safety receptacle 32 is held by a hand of the operator during venipuncture, he or she can see blood entering the flash chamber, which is located forwardly of such safety receptacle, and thereby know that a vein has been successfully penetrated.

As previously indicated, in all embodiments, if the length of the coupling stem, 12a, 28, or 33c, is such that the distance L1, FIGS. 10 and 21, between the release point of the needle-stopping member 11, 23, or 31 and the needle-release actuating point at the rearward end portion of such coupling stem is shorter than the distance L2 between the rearward end of the catheter (13 or 34) and the sharp venipuncturing tip (14a or 30a) of the needle when the catheter and the coupling are in the initial unextended position for advancing the catheter into a punctured vein, the catheter will always cover the used needle until needle-release has been activated.

Needle-stopping member 31 closes flash chamber 30c and, to prevent build-up of air pressure upon entry of blood thereinto, has an air-passing plug 36 therein.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A safety intravenous catheter assembly with retractable needle, comprising an elongate safety receptacle for needle retraction following intravenous catheter emplacement; a catheter having a slim forward end portion for receiving a sharp venipuncturing end portion of an intravenous needle and for intravenous emplacement following needle puncturing of a vein of a patient and having a rearward end portion; an elongate needle received by and having a sharp, venipuncturing end portion protruding forwardly from said forward end portion of the catheter and having a needle stem portion extending backwardly therefrom into said safety receptacle; coupling means securing the catheter to the safety receptacle, said coupling means having a forward portion and an elongate coupling stem portion that extends backwardly into said safety receptacle; means normally removably fastening said catheter to said coupling means, with the rearward face of the former to the forward face of the latter, whereby pushing said catheter forwardly following venipuncture of a vein will emplace said forward end of the catheter in the vein; needle-stopping means positioned within said safety receptacle to normally prevent retraction of said needle; means for automatically releasing said needle-stopping means when the related placement of said coupling means and said safety receptacle is changed to enable displacement of said needle-stopping means from needle-stopping position; and resilient means for automatically forcing retraction of said needle into said safety receptacle upon displacement of said needle-stopping means from needle-stopping position.

2. A safety intravenous catheter assembly according to claim 1, wherein the coupling stem portion provides the means for automatically releasing the needle-stopping means for displacement from its needle-stopping position.

3. A safety intravenous catheter assembly according to claim 1, wherein the needle-stopping means is carried by the rearward end portion of the needle stem.

4. A safety intravenous catheter assembly according to claim 3, wherein the needle-stopping means carries a latching arrangement to hold it in needle-stopping position.

5. A safety intravenous catheter assembly according to claim 3, wherein the stem of the needle is formed as a see-through blood-receiving receptacle constituting a flash chamber.

6. A safety intravenous catheter assembly according to claim 1, wherein the needle within the catheter extends transversely across the line of separation of the coupling from the catheter as a barrier to disengagement of coupling and catheter until retraction of the needle occurs.

7. A safety intravenous catheter assembly according to claim 1, wherein the length of the coupling stem is such that the distance between the needle release point of the needle stopping means and the needle release actuating point at the rearward end portion of the coupling stem is shorter than the distance between the rearward end of the catheter and the sharp venipuncturing tip of the needle when the catheter and the coupling means are in the initial unextended position for advancing the catheter into a punctured vein.

8. A safety intravenous catheter assembly, comprising a catheter; a retractable venipuncture needle protectively encased in the catheter for venipuncture and having a rearwardly extending needle stem; a safety needle-retraction receptacle normally connected to said catheter rearwardly thereof; coupling means releasibly engaging said catheter and having an elongate coupling stem extending into said safety receptacle; needle-stopping means normally held in needle-stopping position within said safety receptacle for automatic release coaction with said coupling stem when relative placement of said safety receptacle and said coupling stem is changed to enable displacement of said needle-stopping means to needle non-stopping position; and resilient means for automatically forcing retraction of said needle into said safety receptacle upon displacement of said needle-stopping means from needle-stopping position.

9. A safety intravenous catheter assembly according to claim 8, wherein the needle-stopping means is a needle-stopping member carried by the needle stem at its rearward end, said needle-stopping member being provided with latch means for latching coaction with latch means provided by the safety needle-retraction receptacle to normally hold said needle-stopping means in needle-stopping position.

10. A safety intravenous catheter assembly according to claim 9, wherein the latch means provided by the needle-stopping member is an outwardly projecting latch member and the latch means provided by the safety needle-retraction receptacle is a receiving recess formed in the safety receptacle and opening into its inner surface, the coupling stem normally extending rearwardly of said needle-stopping member to hold it in latching position but adapted to release said latch means when moved forwardly by the resilient means out of latching position.

11. A safety intravenous catheter assembly according to claim 10, wherein the outwardly projecting latch member and the receiving recess are formed as respective upwardly and backwardly sloping ramp surfaces to facilitate disengagement thereof.

12. A safety intravenous catheter assembly according to claim 11, wherein the safety needle-retraction receptacle has a closed forward end; and wherein the resilient means is positioned between said closed forward end of the safety needle-retraction receptacle and the needle-stopping member for pushing the needle stem and needle rearwardly when the latch means are released from latching positions.

* * * * *